United States Patent [19]

Heinze

[11] Patent Number: 4,636,261

[45] Date of Patent: Jan. 13, 1987

[54] DRY LAKE SYSTEM

[76] Inventor: Richard F. Heinze, 248 White Oak Ridge Rd., Bridgewater, N.J. 08807

[21] Appl. No.: 664,319

[22] Filed: Oct. 24, 1984

[51] Int. Cl.$^4$ .................. C08D 17/02; C04B 14/00
[52] U.S. Cl. ............................ 106/289; 106/300; 106/308 Q
[58] Field of Search .............. 106/289, 308 Q, 300

[56] References Cited

U.S. PATENT DOCUMENTS

| | | | |
|---|---|---|---|
| 2,079,548 | 5/1937 | Crossley et al. | 106/289 |
| 3,663,284 | 5/1972 | Stancioff et al. | 106/300 |
| 3,981,984 | 9/1976 | Signorino | 106/193 J |
| 3,992,215 | 11/1976 | Su et al. | 106/287.14 |
| 4,224,080 | 9/1980 | Chambers et al. | 106/308 Q |

FOREIGN PATENT DOCUMENTS 2065691 7/1981 United Kingdom .

OTHER PUBLICATIONS

Chem. Abstract 52: 15839i, Soledad Paz Soldànc.

Primary Examiner—Theodore Morris

[57] ABSTRACT

The invention relates to a dry pigment composition used for producing a film coating or sugar coating of such items as pharmaceutical tablets, confectionary pieces and the like. The invention also has valuable application to the internal coloring of candy. The composition comprises powdered edible pigment particles and a dispersing agent which prevents agglomerization and facilitates dispersion into solution. A typical dry film coating composition comprises lake pigment particles and a small quantity of sodium citrate.

14 Claims, No Drawings

DRY LAKE SYSTEM

THE BACKGROUND OF THE INVENTION

This invention relates to the art of color coating such edible consumer products as pharmaceutical tablets, confectionary pieces, and the like. More particularly, the invention is directed to a dry pigment composition used for making a color coating suspension. However, the invention also has application to the internal coloring of products, for example, the internal coloring of candy.

The color coating of products can be advantageously accomplished by applying a film forming pigment containing suspension, which typically includes the presence of a film forming polymer. In other cases, the color coating of products is appropriately accomplished by applying a sugar syrup suspension containing an aqueous dispersion of pigment.

The general techniques of film coating and sugar coating are known in the prior art. For example, U.S. Pat. No. 2,954,323 to Endicott et. al. discloses the improved efficiency of the film coating process and the superior coating properties of the products made thereby.

The coating suspensions used in film coating or sugar coating are typically made from commercially available pigment suspensions, which are conventionally concentrated non-aqueous dispersions of lake pigments, usually including a colloid such as polyvinylpyrollidone for maintaining the pigment in dispersion. The pigment dispersions are typically stirred into a larger volume of polymer solution or sugar solution to form the color coating suspensions. Examples of such pigment dispersions and their use are described in U.S. Pat. No. 3,981,984 to Signorino. The U.S. application to Heinze et. al., filed on the same day as this application, discloses an aqueous pigment suspension, including a viscosity lowering agent such as sodium citrate or similar salts of carboxylic acids.

The purpose of the present invention was to obtain a dry composition, rather than a liquid pigment suspension, which could be added directly to a polymer solution or sugar syrup solution to form a color coating suspension. Dry compositions have heretofore not been widely used because of the difficulties involved with their application. Dry compositions have a tendency to agglomerate and resist dispersion in solution. This can result in a poor quality coating, since the coating, in the form of a very thin film, must be uniform and consistent from one batch of tablets to the next. It is desired to obtain a coating exhibiting a smooth, polished, and elegant appearance which requires well dispersed pigment particles. However, this has been difficult to obtain with a dry composition, and the results have been unsatisfactory.

U.K. Patent Application No. GB 2065691A, by Porter et. al., published on July 1, 1981, discloses a method of making a dry film coating composition which comprises the steps of mixing a polymer powder, such as methylcellulose, and pigment particles in a blender, adding a placticizer such as polyethylene glycol to the blender containing the polymer-pigment mix, and mixing until the combined mix is throughly blended. A surfactant or a flow aid is optional.

The present applicant has invented a dry composition for use in film coating or sugar coating, which comprises pigment particles and a small quantity of what is referred to as a dispersing agent, which has an extraordinary effect on the pigment particles. The dispersing agent effects the pigment particles in the dry state as well as facilitating dispersion into solution. The dry composition forms uniform small particles that maintain a striking degree of separation. The particles do not agglomerate, and as a result, a more uniform coating is obtained. The solubility of the composition in the film forming solution increases by a factor of five or more. The phenomenon known as specking, caused by larger sized pigment particles that do not disperse, is rendered insignificant or absent.

The present composition need not contain the high levels of polymer or plasticizer required in U.K. Patent Application No. GB 2065671A, referred to above. The present composition is useful in both aqueous and organic film coating and in sugar coating as well. The composition readily disperses in liquid as a result of the dispersing agent.

The advantage of a dry pigment composition in comparison to a liquid pigment suspension is great. The dry pigment composition would have virtually unlimited stability and storage life. There is no danger of the pigment particles settling out and hardening, as is liable to occur with pigment suspensions. The necessity for preservatives and the danger of microcontamination is reduced or avoided. Since the composition weighs considerably less than the liquid composition, the expense of shipment and the cost of the product is reduced. The presence of inflammable or deleterious organic solvents is obviated.

A primary object of the present invention is to obtain a dry pigment composition capable of use in a film forming solution or sugar solution.

Another object of the present invention is to obtain a dry pigment composition capable of use for the internal coloring of candy such as jelly beans.

Another object of the present invention is to obtain a dry pigment composition which readily disperses in solution.

A further object of the present invention is to obtain a dry pigment composition which does not agglomerate or form clumps or specks in solution.

A further object of the present invention is to obtain a dry pigment composition which exhibits relatively small and uniform particles.

A further object of the present invention is to obtain a dry pigment composition which forms a coating which is smooth and elegant in appearance.

A further object of the present invention is to obtain a dry pigment composition which has high stability and long storage life.

The above and other objects of the present invention will become apparent from a reading of the following detailed description of the invention and the preferred embodiments thereof.

DETAILED DESCRIPTION OF THE INVENTION

The pigment suspension of the present invention comprises a mixture of a pigment and a dispersing agent.

The pigments suitable for use in the context of the present invention include pigment hydroxide lakes, which are dyes combined with a metal hydrate substratum. A variety of lakes, including lakes incorporating azo, triphenylmethane, fluorescein, and sulfonated indigo dyes, are suitable in the present invention. Natural lakes such as carmine are suitable. FD&C lakes are suitable for application in food, drug, and cosmetic products. D&C lakes such as D&C Red 27 are suitable for pharmaceutical and cosmetic application.

Lakes have been developed with a wide range of strengths. For food and confectionary applications, the mid-range dye content lakes are the most useful. These lakes are manufactured by Crompton & Knowles Corporation of Fairlawn, New Jersey (hereinafter referred to as "C&K"), and Warner-Jenkinson Manufacturing Company of Saint Louis, Missouri (hereinafter referred to as "W-J"). For example, the following pigments are commercially available from C&K or W-J:

| Yellow | #6/40% |
|---|---|
| Yellow | #5/36% |
| Blue | #1/11% |
| Blue | #2/39% |
| Red | #40/40% |
| Red | #27/36% |
| Red | #3/40% |

A 50/50 combination of C&K and W-J lakes may be preferrable. In general, it has been found that W-J lakes tend to have a higher tint, but may cause thickening. By using a mixture of W-J and C&K lakes, both a high tint and non-thickening is more readily obtained. Of course, developments and changes in the lakes by their manufacturers may require a reassessment, as would be understood by those skilled in the art, of the properties of a particular brand in regard to use in the present invention.

The dispersing agent is most effectively a salt of an organic, carboxyl containing compound and mixtures thereof with the acid form. Preferred dispersing agents include salts of compounds having one to four carboxylic groups. Dispersing agents include, but are not limited to salts of adipic acid, benzoic acid, citric acid, fumaric acid, succinic acid, maleic acid, lactic acid, tartaric acid, ascorbic acid, and propionic acid and mixtures with the acid thereof. Trisodium phosphate has been found to work in some cases as a dispersing agent, but in general not as well as the above mentioned organic, carboxylic containing compounds.

In general, the dispersing agents must, at least partly, be in the salt form. A 50/50 combination of the salt and acid is suitable. For example, sodium citrate, by itself, or a mixture of sodium citrate and citric acid, produces excellent results. It is surmised that the dispersing agent complexes or is absorbed by the lake pigment particles. Due to the wide variety of dyes present in lake pigments, it is further surmised that the metal hydroxide substrate of the FD&C lakes may function in the complexing of the dispersing agent. The resulting complex is believed to have electronic properties such that they repell another such complex, thereby resulting in readily and uniformly dispersed pigment particles.

The presence of one of the dispersing agents results in a dramatic change in the properties exhibited by the pigment composition, both in the dry form and in solution. The composition readily disperses in solution and neither agglomerates nor clumps. The dispersing agent is preferably present in an amount of 0.005 to 5 percent by weight in the mixture. The agent is more preferably present in an amount of 0.02 to 3.0 percent and most preferably, in an amount of 0.1 to 1.5 percent. In many cases, even a relatively very small amount of dispersing agent can drastically and favorably effect the properties of the composition.

The following Examples are intended to illustrate the invention.

EXAMPLE 1

In a blender, the following components were weighed out and mixed:

| Component | Weight |
|---|---|
| Titanium dioxide 3328 | 49.99 g |
| Red 40/40 | 24.99 g |
| Yellow 6/40 | 24.99 g |
| Sodium Citrate | 1.50 g |

This composition readily dispersed in a sugar solution composed of a mixture of water and sucrose in a ratio of 3 to 7. This dispersion exhibited excellent coating properties.

EXAMPLE 2

A drawdown is a test used to simulate the coating process. A few drops of the suspension to be tested are placed in a line across a glass plate. Then a metal arm which is spaced a fraction of a millimeter from the glass plate is used to draw the suspension across the plate so as to produce a thin film. By examining this thin film, non-uniformity or other possible defects in the suspension can be observed. If the drawdown is clear and uniform, it is expected that the suspension will produce a good coating.

In a blender, the following components were weighed out and mixed:

| Component | Weight |
|---|---|
| Blue 2/39 | 50 g |
| Titanium dioxide 3328 | 50 g |
| Sodium Citrate | 0.5 g |

This composition was dispersed in a sugar syrup solution, Drawdowns of the dispersion were made to determine the degree of dispersion and the unformity of the dispersion. The results were excellent.

COMPARATIVE EXAMPLE 3

The composition of Example 1 was repeated, except that sodium citrate was not included. The composition was as follows:

| Component | Weight |
|---|---|
| Titanium dioxide 3328 | 50 g |
| Red 40/40 | 25 g |
| Yellow 6/40 | 25 g |

The composition of Example 3 was compared to the composition of Example 1. It is noted that the lakes of Examples 1 and 3 were obtained from the same lot so that the effect of the presence of the dispersing agent could be more accurately evaluated. The comparison involved side-by-side drawdowns and microscopic comparison of the solutions. The composition of Example 1 was found to be significantly superior to the composition of Example 3 in every respect. The dry blend with sodium citrate exhibited uniformly small particles, whereas the dry blend without sodium citrate exhibited agglomerates. Moreover, the particles present in the composition of comparative example were clearly not as uniform and relatively larger in average diameter.

With respect to dispersing, the effect of the addition of sodium citrate was also noticeable. The dry blend with sodium citrate readily dispersed in about 1 to 2 minutes. In contrast, the dry blend without sodium citrate required at least ten minutes to mix into the solution.

EXAMPLE 4

The following components were weighed out and blended:

| Component | Weight |
| --- | --- |
| Titanium dioxide 3328 | 20 g |
| Yellow 6/39 | 20 g |
| Sodium Citrate | 2 g |

This composition of the present invention was compared to the composition of comparative Example 5 below.

COMPARATIVE EXAMPLE 5

The dry blend of the present invention as illustrated by Example 4 was compared to the use of a dry blend not containing sodium citrate. The lakes in both examples were taken from the same lot. This comparative example consisted of the following:

| Component | Weight |
| --- | --- |
| Titanium dioxide | 20 g |
| Yellow 6/39 | 20 g |

The compositions of Example 4 and Comparative Example 5, respectively, were added to a 70/30 sugar syrup solution at a weight concentration of 1.50 percent. Drawdowns and visual microscopic observation were made of the respective dispersions.

It was found that the dispersion made with the composition of Example 4 exhibited dispersed particles that were significantly smaller and finer in size. The dry blend without sodium citrate required at least five times as long to disperse in the sugar syrup solution.

COMPARATIVE EXAMPLE 6

The following components were weighed out and mixed:

| Component | Weight |
| --- | --- |
| Titanium dioxide 3328 | 15.00 g |
| Yellow 6/39 | 15.00 g |
| Polyvinylpyrollidone | 1.00 g |
| Sugar | 41.40 g |
| Distilled water | 27.60 g |

A quantity of this mixture was added to a 70/30 sugar water solution. The suspension was mixed well for one half hour using a magnetic stirrer and heating to 80° C. Drawdowns and microscpopic observations were made of the mixture.

This dispersion was found to be inferior to the composition of the present invention exemplified by Example 4 above. In comparison, the dispersion of Example 4 showed particles of significantly smaller and finer size.

The composition of the present invention may contain additional additives. For example, in order to make the composition dustless, a non-dusting additive such as propylene glycol, glycerine, or dioctyl sodium sulfosuccinate (DSS) may be included in an effective amount of about five percent.

It is to be understood that the foregoing detailed description and preferred embodiments are merely given by way of illustration, and that modifications may be made, within the skill of the art, without departing from the scope and spirit of the invention.

We claim:

1. A storage stable composition capable of use in color coating or internal coloring of products, comprising a dry mixture of pigment selected from the group consisting of carmine, a D&C lake, or an FD&C lake, and additionally 0.005 to 5.0 percent, at least partly in the salt form, of an organic compound containing one to four carboxylic acid groups or a salt of phosphoric acid.

2. The composition of claim 1, wherein the dispersing agent is the salt of an organic compound containing one to four carboxylic acid groups.

3. The composition of claim 1, wherein the dispersing agent is selected from the group consisting of the salts of tartaric acid, citric acid, fumaric acid, adipic acid, maleic acid and mixtures with the acid thereof.

4. The composition of claim 1, wherein the dispersing agent is selected from the group consisting of salts of tartaric acid, citric acid, and mixtures with the acid thereof.

5. The composition of claim 1, wherein the dispersing agent is trisodium phosphate.

6. The composition of claim 2 containing 0.1 to 0.5 percent of a salt of an organic compound containing at least one carboxylic acid group or a salt of phosphoric acid.

7. The compositioin of claim 5, comprising a pigment and 0.02 to 3.0 percent of a salt of an organic compound containing at least one carboxylic acid group or a salt of phosphoric acid.

8. The composition of claim 6, wherein the pigment is a D&C or FD&C lake.

9. The composition of claim 6, wherein the dispersing agent is the salt of an organic compound containing one to four carboxylic acid groups.

10. The composition of claim 6, wherein the dispersing agent is selected from the group consisting of the salts of tartaric acid, citric acid, fumaric acid, adipic acid, maleic acid and mixtures with the acid thereof.

11. The composition of claim 6, wherein the dispersing agent is selected from the group consisting of salts of tartaric acid, citric acid, and mixtures with the acid thereof.

12. The composition of claim 6, wherein the dispersing agent is trisodium phosphate.

13. The composition of claim 12, wherein the non-dusting additive is selected from the group consisting of propylene glycol, glycerine.

14. The composition of claim 6, wherein the pigment is carmine.

* * * * *

UNITED STATES PATENT AND TRADEMARK OFFICE
CERTIFICATE OF CORRECTION

PATENT NO. : 4,636,261

DATED : January 13, 1987

INVENTOR(S) : Richard F. Heinze

It is certified that error appears in the above-identified patent and that said Letters Patent is hereby corrected as shown below:

On the title page, the following should be inserted:

--[73]  Assignee:  Crompton & Knowles Corporation, New York, N. Y. --

Signed and Sealed this

Eleventh Day of August, 1987

*Attest:*

DONALD J. QUIGG

*Attesting Officer*  *Commissioner of Patents and Trademarks*